(12) United States Patent
Muckler

(10) Patent No.: US 6,983,582 B1
(45) Date of Patent: Jan. 10, 2006

(54) STALK STRENGTH TESTER

(76) Inventor: Gregory A. Muckler, 5685 E. 156th St. North, Grinnell, IA (US) 50112

(*) Notice: Subject to any disclaimer, the term of this patent is extended or adjusted under 35 U.S.C. 154(b) by 165 days.

(21) Appl. No.: 10/631,459

(22) Filed: Aug. 1, 2003

(51) Int. Cl.
*A01D 75/18* (2006.01)

(52) U.S. Cl. .............................................. 56/1
(58) Field of Classification Search .............. 73/81, 73/838; 56/1, 10.2 R, 10.2 A–10.2 F
See application file for complete search history.

(56) References Cited

U.S. PATENT DOCUMENTS

| | | | |
|---|---|---|---|
| 570,553 A | 11/1896 | Hunter | |
| 855,754 A | 6/1907 | Buschmann | |
| 1,141,562 A | 6/1915 | Law | |
| 1,670,685 A | * 5/1928 | Marks | 73/81 |
| 1,942,982 A | * 1/1934 | Schneider | 73/81 |
| 2,421,449 A | * 6/1947 | Zuber | 73/81 |
| 2,570,321 A | 10/1951 | Christoffer | |
| 2,816,439 A | * 12/1957 | Hayes | 73/81 |
| 2,851,878 A | * 9/1958 | Maule | 73/838 |
| 3,223,189 A | 12/1965 | Robbins | |
| 4,785,897 A | 11/1988 | Keinert, Jr. | |
| 4,954,783 A | 9/1990 | Spry | |
| 5,044,210 A | 9/1991 | Kuhn et al. | |

* cited by examiner

*Primary Examiner*—Árpád Fábián Kovács
(74) *Attorney, Agent, or Firm*—G. Brian Pingel; Camille L. Urban

(57) ABSTRACT

The stalk strength tester of the present invention includes an internal shaft and an external shaft in telescopic relationship. Pivotally associated with the upper end of the internal shaft is a trough-like stalk cradle. A set of measurement markers are on the upper end of the internal shaft and a rubber ring is around the internal shaft and abuts the external shaft. Associated with the other end of the internal shaft is a tension member. A tension adjustment structure is provided for adjusting the tension in the tension member. In operation, a stalk is positioned into the cradle and the tester is pushed against it. The internal shaft telescopically slides against the tension member and into the external shaft until the cradle pivots at which time the rubber ring remains in a position relative to one of the markers as an indicator of the tension measured.

12 Claims, 6 Drawing Sheets

STALK STRENGTH TESTER

BACKGROUND OF THE INVENTION

1. Field of the Invention

The present invention relates in general to a device for determining stalk strength of crop plants and, more specifically, to a stalk tension measuring device which is calibrated, preferably spring loaded, and equipped to measure tension without breaking the stalks tested.

2. Description of the Prior Art

It is known in the art to use devices to assist in determining stalk strength and moisture levels in plants. Such information can be used to help determine readiness of the plants for harvest or to simply examine and compare the stalk strength of plants.

U.S. Pat. No. 4,954,783 discloses a corn moisture tester, which operates by enclosing an ear of corn in a close-able sleeve. Upon closure of said sleeve around the ear of corn, conductor blades or electrodes pierce the kernels and the electrical conductivity is measured. This conductivity provides a measure of the moisture in the kernels but does not allow testing of moisture or strength of stalks.

A device for testing the strength of plant stalks is disclosed by U.S. Pat. No. 5,044,210. Here, the device includes a frame with an upright member attached to a spring loaded horizontal arm secured to a moving vehicle. As the vehicle moves along a row of plants, the arm engages each plant. If the plant is strong enough it will bend and not break or the arm will pivot rearwardly on its way past the stalk and then spring back to its position before engaging the next plant. If it is not strong enough, the stalk will break. A measurement of the strength of the group of stalks is obtained by counting the number of broken stalks in the row.

Of course, tension can be measured in other ways. Although other devices have been disclosed for measuring tension in general, such as weighing scales, the disclosures of these devices do not contemplate their use for measuring tension in plant stalks nor would these devices be aperable for that purpose. For example, U.S. Pat. No. 570,553 granted in 1896 discloses a portable weighing scale which includes a hollow handle in telescopic relationship with a tube. One end of the tube is attached to a spring in the handle, the other to a scoop positioned above the handle. The weight of material placed in the scoop can be taken by reading the position of the tube against a graduated scale as said tube is pushed downward into the handle by the weight of the material. However, this device would not work for stalk strength measurements because it is not designed to be hand-held, or used horizontally or to press, but not break, stalks of a given strength.

Other simple weighing scales have been patented that disclose devices against which is hung the item to be weighed, rather than weighing the item by placing it on or above the scales. Examples include U.S. Pat. Nos. 855,754; 3,223,189; 1,141,562; 2,570,321; 4,785,897. Most of these include a first member in telescopic or slidable relationship with another. Said first member is then associated with the item to be weighed such that the weight of the item acts to move the first member against a tension element. The relative position of the first member is then compared to its resting position to obtain a measure of the weight of the item.

None of the above-mentioned devices provide a device which allows measurement of the strength of plant stalks. What was needed was a device that can be used to measure stalk strength in the field on vertically growing stalks without breaking the stalks, by a conveniently hand-held device, and in a way that is calibrated such that measurements can be compared across time and location. Such a device would provide a way for a researcher or farmer to compare the stalk strengths of different varieties or cultivars, at various stages in the growing season. If recorded, such data could be used to evaluate the stalk characteristics of these plants in various climates, geographic locations, moisture patterns, and fertilizer or herbicide/pesticide applications.

The present invention provides a light weight, hand-held device. This device can be calibrated to meet standards such that even if multiple devices are used by multiple people in multiple places, measurements so taken will be consistent and have meaning. In addition, the present invention can be provided with differing tension elements and in sizes adapted to the size and general strength expected for the stalks of a given crop. Finally, the present invention is designed to be simply and effectively used in the field on growing plants and with a minimum of stalk breakage.

SUMMARY

The present invention provides a stalk strength tester which is hand-held, can be calibrated, and minimizes the breakage of stalks being tested. The tester is constructed using an internal shaft and an external shaft in telescopic relationship with one another. Associated with the internal shaft is a tension element which can be calibrated such that a plurality of testers can be depended upon to provide consistent measurements. The telescopic relationship of the internal and external shaft is maintained by inserting a securing element through a slot in the external shaft and affixing it to the internal shaft while allowing the shafts to be remain slidable relative to one another.

Near an upper end of the internal shaft and above said external shaft when in resting position is a set of measurement markings and a frictionally engaged slidable marker. Pivotally attached to the upper end of the internal shaft is a trough-like cradle. The cradle's trough-like shape is used to provide alignment of the generally vertically growing stalk the strength of which is to be measured and the pivotal nature of the cradle allows the stalk to bend and slide out of the cradle just prior to its breaking point.

Upon application of the cradle of the tester to a stalk, the internal shaft is pushed against the tension member and slides away from its resting position and inside the external shaft until the stalk bends and the cradle pivots. At that point, the frictionally engaged slidable marker has been moved relative to the set of measurement markers to a place relative to the strength of the stalk. As the internal shaft is returned to its resting position, the slidable marker remains in place to indicate the strength measurement of the stalk.

Other objects, features, and advantages of the present invention will be readily appreciated from the following description. The description makes reference to the accompanying drawings, which are provided for illustration of the preferred embodiment. However, such embodiment does not represent the full scope of the invention. The subject matter which the inventor does regard as his invention is particularly pointed out and distinctly claimed in the claims at the conclusion of this specification.

DESCRIPTION OF THE PREFERRED EMBODIMENT(S)

Figure 1:
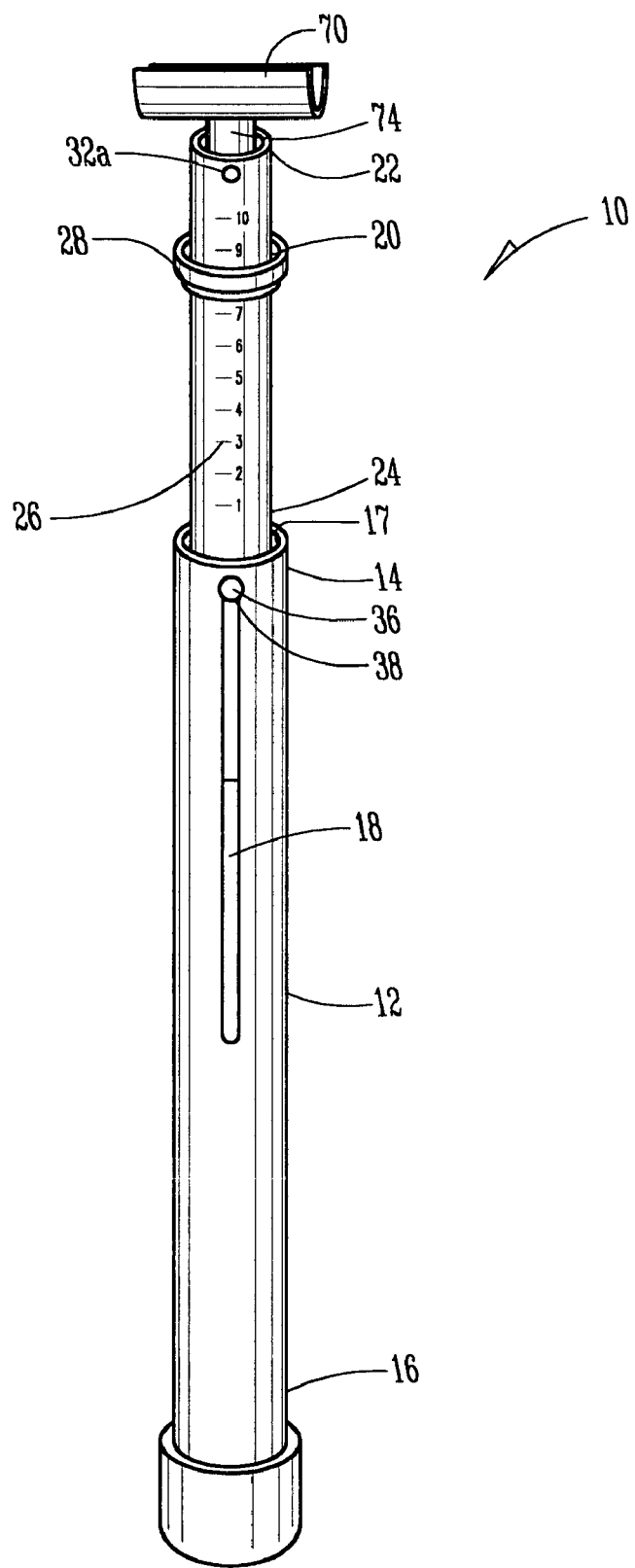
FIG. 1 is perspective view of a first preferred embodiment of the stalk strength tester of the present invention.

Referring to FIG. 1, a first embodiment of the Stalk Strength Tester of the present invention is shown generally at 10. The tester 10 comprises an external shaft 12 with a first end 14, a second end 16, an interior 17, and a lengthwise slot 18, an internal shaft 20 including an upper end 22, a lower end 24, a set of measurement markings 26, and a slidable marker 28. In the preferred embodiment, the internal shaft 20 includes a set of opposing apertures 30a and 30b and a set of aligned apertures 32a and 32b.

Figure 2:
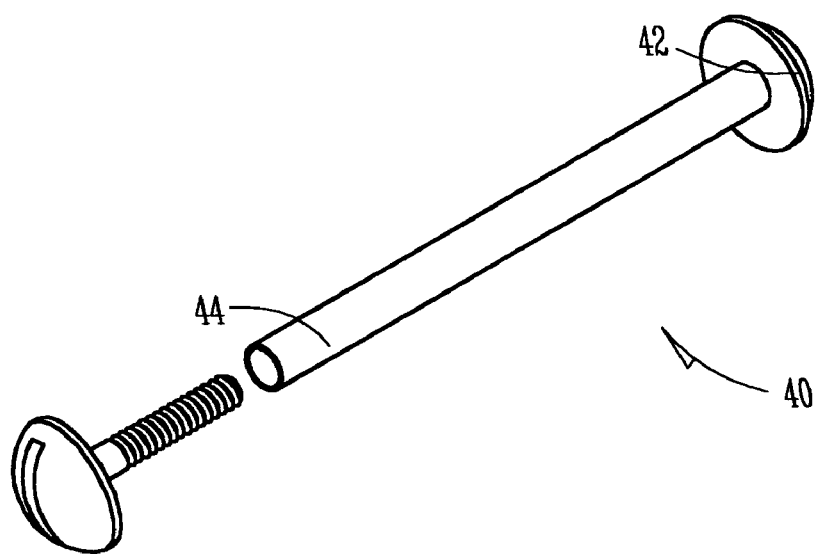
FIG. 2 is a perspective view of a pin used in a second preferred embodiment of the present invention.

The internal shaft 20 and the external shaft 12 are in telescopic relationship with one another. Means 34 for slidably maintaining the telescopic relationship of the internal shaft 20 and external shaft 12 is provided. In the first embodiment of the present invention, the means 34 comprises a first pin 36 affixed to the internal shaft 20 and protruding through the lengthwise slot 18 in the external shaft 12 and slidably secured by a head 38. In a second embodiment of the present invention, a rod 40 with two ends 42 and 44, shown best in FIG. 2, is inserted through the two opposing apertures 30a and 30b in the internal shaft 20 and through two slots 18a and 18b (not shown) which are positioned opposite one another on the external shaft 12. The ends 42 and 44 of the rod 40 are then slidably secured in the slots 18a and 18b. Although both of the preferred embodiments incorporate the use of a pin and slot arrangement to serve as the means 34, such arrangement is not essential to the present invention as there are other known types of structures for providing a telescopic relationship between the shafts 12 and 20, for example the use of limit of movement spacers located within the interior 17 of the shaft 12.

Figure 3:
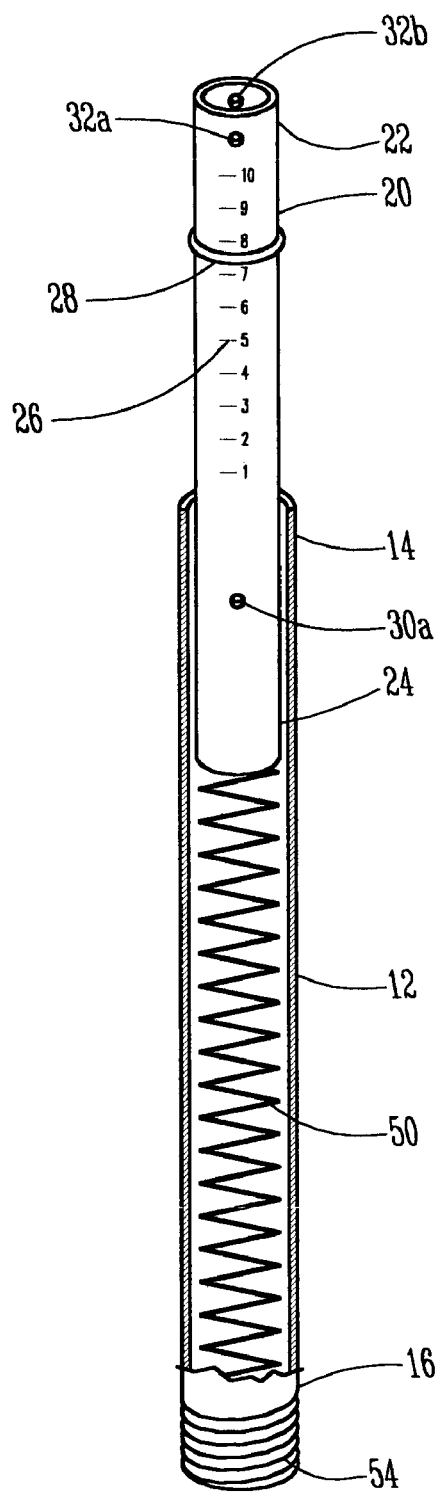
FIG. 3 is a partial cross section view showing the arrangement of elements in the interior of the stalk strength tester of FIG. 1.
Figure 5:
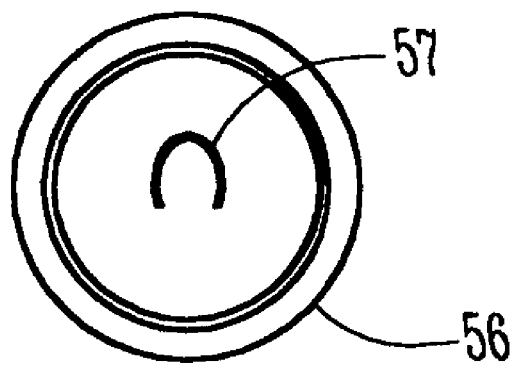
FIG. 5 is a plan view of the endpiece of FIG. 4 showing means to fixedly associate a tension member.
Figure 4:
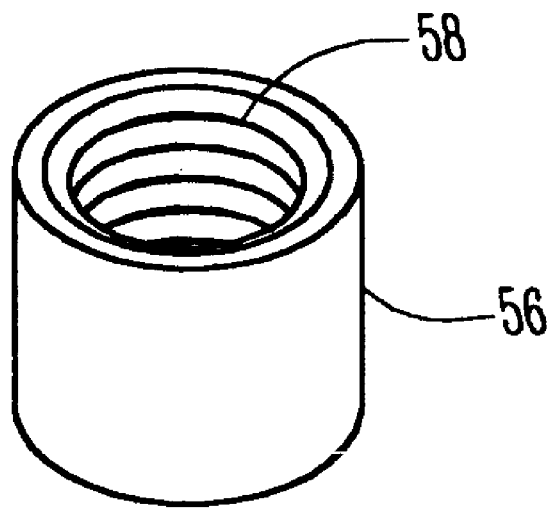
FIG. 4 is a perspective of an endpiece of the stalk strength tester of FIG. 1.

As shown by FIG. 3 is the arrangement of elements in the interior 17 of the external shaft 12. The lower end 24 of the internal shaft 20 is associated with a tension member 50 and the second end 16 of the external shaft 12 is also associated with the tension member 50 to keep it in place. In the preferred embodiment wherein the tension member 50 is a coiled spring as shown in FIGS. 3–5, means 52 for calibrating the tension member 50 are provided and, in a first modification, include the second end 16 of the external shaft 12 upon which are external threads 54 and an endpiece 56 with means 57 (shown in FIG. 5) for fixedly associating the tension member 50. The endpiece 56 upon which are internal mating threads 58 is fitted over the second end 16 of the external shaft 12. As the endpiece 56 is screwed onto the end 16, the internal threads 58 of the endpiece 56 coact with the threads 54 on the external shaft 12, and the tension member 50 is tightened. The tightening of the tension member 50 serves as the means 52 for calibrating the tension member 50.

Figure 9:
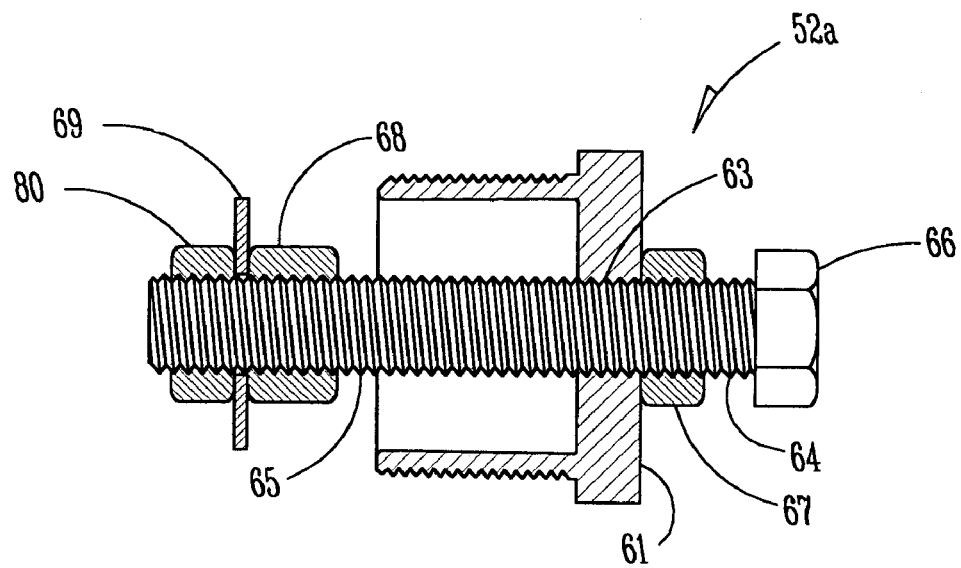
FIG. 9 is a side view of the tension adjusting means of FIG. 8.
Figure 8:
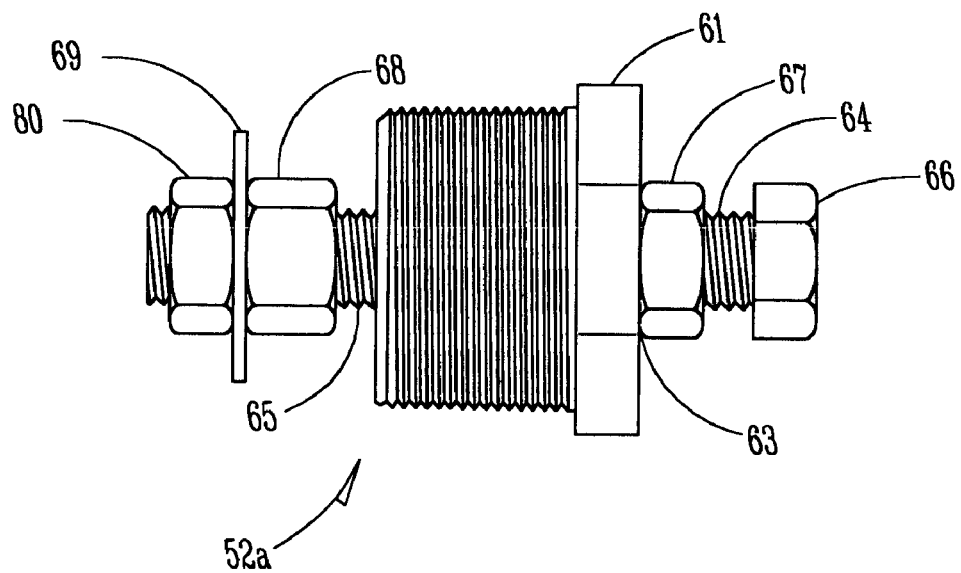
FIG. 8 is a cross section of a modified means for adjusting the tension member of the tester of FIG. 1.

In another modification, as shown in FIGS. 8 and 9, a means 52a is utilized for calibrating the tension member 50 and is designed to coact with the second end 16 of the external shaft 12 which is modified to have internal threads rather than the external threads 54. An endpiece 61 comprises part of the means 52a and is adapted for adjustably compressing the tension member 50 to a desired tension. The endpiece 61 has a threaded aperture 63 through which a bolt 64 with a threaded end 65 and a head 66 protrudes. Said head 66 of said bolt is stabilized against the endpiece 61 by use of a tightened nut 67. On the outer portion of the threaded bolt end 65 are a second nut 68, a washer 69 larger than said tension member 50, and a third nut 80. Said second nut 68 and said third nut 80 flank the washer 69 such that the second and third nuts 68 and 80 can be turned on said threaded end 65 to a position wherein the tension member 50 is shortened or lengthened to effect the tension desired. The end piece 61 has external threads to mate with the internal threads of the modified external shaft 12 to attach the endpiece 61 thereto.

Figure 6:
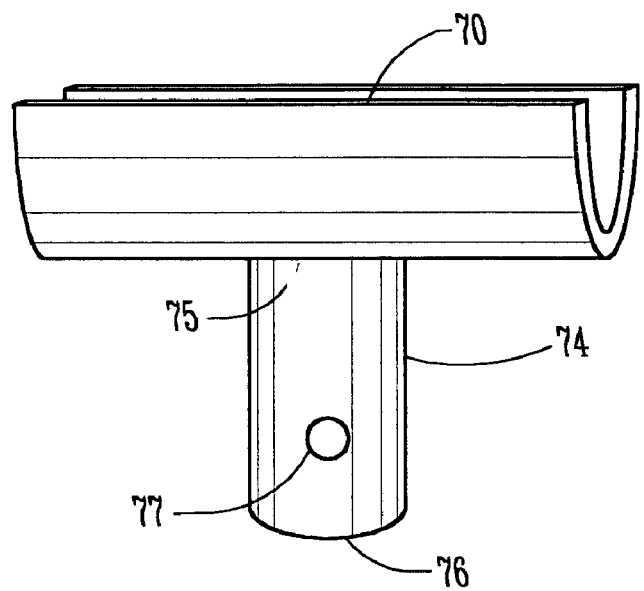
FIG. 6 is a perspective view of a trough-like stalk cradle that forms part of the present invention of FIG. 1.
Figure 7:
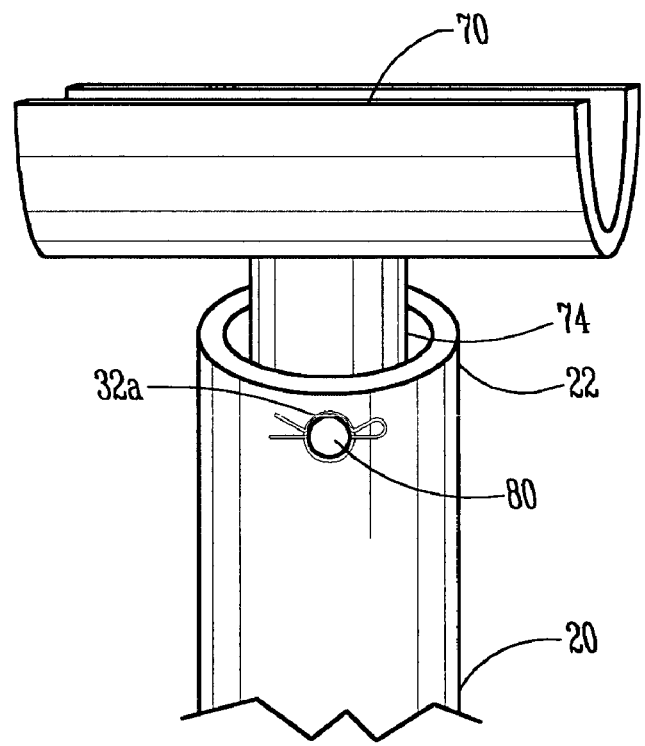
FIG. 7 is a perspective view of one end of the stalk strength tester of FIG. 1 with the stalk cradle.

Turning now to FIGS. 6 and 7, on the upper end 22 of the internal shaft 20 is pivotally associated a trough-like stalk cradle 70. Means 72 for pivotally associating the stalk cradle 70 with the upper end 22 of the internal shaft 20 are provided and in the preferred embodiment, the means 72 comprise a foot member 74 including a first end 75 attached to the cradle 70 and a second end 76 with an aperture 77 inserted into the upper end 22 of the internal shaft 20. The second end 76 of the foot member 74 is pivotally secured to the internal shaft 20 with a cotter pin 80 which is inserted through the aligned apertures 32a and 32b on the upper end 22 of the internal shaft 20 and through the aperture 77 in the foot member 74.

The operation of the preferred embodiment starts with the tester 10 in a resting position, without pressure on the tension member 50. The slidable marker 28 should be moved to rest against the first end 14 of the external shaft 12 and aligned with one of the set of measurement markers 26. Next, a stalk is positioned into the trough-like stalk cradle 70 and the tester 10 is pushed against the stalk; the internal shaft 20 is pressed against the tension member 50 and moves telescopically into the external shaft 12 thereby moving the slidable marker 28 toward the outer end of internal shaft 20. When the stalk is near its breaking point, it will bend and the stalk cradle 70 will pivot, releasing the stalk. At that time, the internal shaft 20 moves telescopically outward from the external shaft 12 back to the resting position and the slidable marker 28 is left at a position corresponding to the highest tension borne by the stalk as indicated by one of the set of measurement markers 26. In the preferred embodiment, the slidable marker 28 is a rubber ring frictionally, yet slidably, engaged with the internal shaft 20.

To calibrate the tester 10, the stalk cradle 70 is pushed against a weight calibrating device (not shown) and the endpiece 56 turned until the slidable marker 28 is positioned at one of the set of measurement markers 26 which was preselected. This process can be repeated with a number of different testers in order to calibrate them one with the other and, therefore, to be able to compare measurements taken by a plurality of testers.

Thus, the present invention has been described in an illustrative manner. It is to be understood that the terminology that has been used is intended to be in the nature of words of description rather than of limitation.

Many modifications and variations of the present invention are possible in light of the above teachings. For example, as described earlier, the telescopic relationship of the shafts can be maintained in a number of different ways. In addition, there are many ways the tension member can be calibrated, or the spring mechanism can be substituted with an electronic function for providing the measurements provided by the tester 10. One such possible electronic modification would be the use of a load cell secured in the external shaft 12 to engage the lower end 24 of the internal shaft 20 when pressure on the tester 10 is applied. A digital display can be associated with the load cell to provide a visual readout of stalk measurements. Therefore, within the scope of the appended claims, the present invention may be practiced otherwise than as specifically described.

What I claim is:

1. A stalk strength tester comprising:
   (a) an external shaft comprising a first end, and a second end;
   (b) an internal shaft comprising an upper end, a lower end, a set of measurement markings near said upper end, and a slidable marker for retaining a strength reading;
   (c) a tension member associated with said lower end of said internal shaft;
   (d) said tension member and said lower end of said internal shaft in telescopic relationship with said external shaft wherein said tension member is positioned within said second end of said external shaft and said internal shaft is positioned such that said measurement markings are above and outside said external shaft;
   (e) means for slidably maintaining said internal shaft and said external shaft in telescopic relationship;
   (f) a trough-like stalk cradle for pivotally aligning a stalk for strength measurement; and
   (g) means for pivotally associating said trough-like stalk cradle with said upper end of said internal shaft.

2. A stalk strength tester as claimed in claim 1 wherein said external shaft, said internal shaft, and said trough-like stalk cradle are made of PVC pipe, and said tester further includes means for calibrating said tension member.

3. A stalk strength tester as claimed in claim 1 wherein said slidable marker for retaining a strength reading comprises a rubber ring in frictional relationship with said internal shaft, positioned above said first end of said external shaft such that said slidable marker is moved relative to said set of measurement markings when said internal shaft slides telescopically into said external shaft and retains that position when said internal shaft slides back out of said external shaft.

4. A stalk strength tester as claimed in claim 3 wherein said tension member comprises a coiled spring.

5. A stalk strength tester as claimed in claim 1 wherein said external shaft has at least one axially aligned slot and wherein said means for slidably maintaining said internal shaft and said external shaft in telescopic relationship comprises a pin inserted through said at least one slot, affixed to said internal shaft, and secured within said at least one slot by a head within said slot.

6. A stalk strength tester as claimed in claim 1 wherein said external shaft further comprises two slots, said internal shaft further comprises two opposing apertures, and said means for slidably maintaining said internal shaft and said external shaft in telescopic relationship comprises a rod inserted through said two slots and said two opposing apertures in said internal shaft and slidably secured outside said external shaft.

7. A stalk strength tester as claimed in claim 4 wherein said means for calibrating said tension member comprises external threads on said second end of said external shaft, an endpiece with internal threads and which fits over said second end of said external shaft, means for fixedly associating said tension member with said end piece such that by turning said endpiece on to said external threads on said second end of said external shaft, the tension of said tension member is varied.

8. A stalk strength tester as claimed in claim 1 wherein said internal shaft further comprises two aligned apertures near said upper end, and means for pivotally associating said trough-like stalk cradle with said upper end of said internal shaft comprises a foot member including an aperture, a first end fixedly attached to said trough-like cradle, and a second end inserted in said upper end of said internal shaft and pivotally secured therein by a cotter inserted through said aperture in said foot member and said two aligned apertures in said internal shaft.

9. A stalk strength tester comprising:
   (a) an external shaft comprising a first end, a second end which is closed, and an internal shaft comprising an upper end and a lower end;
   (b) means for slidably maintaining said internal shaft in telescopic relationship with said external shaft comprising at least one lengthwise slot in said external shaft through which a pin is inserted and also fixedly attached to said internal shaft;
   (c) a rubber ring in frictional relationship with said internal shaft and abutting said external shaft such that said ring is moved to and retains a new position when said internal shaft is telescopically moved from a first position relative to said external shaft and then returned to said first position;
   (d) a tension member comprising a coiled spring providing tension associated with said second end of said external shaft and with said lower end of said internal shaft; and
   (e) a trough-like stalk cradle pivotally associated with said upper end of said internal shaft for pivotally aligning a stalk for strength measurement.

10. A stalk strength tester comprising:
    (a) an external shaft comprising a first end, a second end, two slots wherein said second end is equipped with external threads;
    (b) an internal shaft comprising an upper end with a set of opposing apertures, a set of aligned apertures, a set of measurement markings and a slidably and frictionally engaged ring near said upper end, and a lower end;
    (c) means for slidably maintaining said external shaft and said internal shaft in telescopic relationship with one another comprising a rod inserted through said set of opposing apertures on said internal shaft and through said two slots on said external shaft and slidably securing said rod in said slots;
    (d) an endpiece comprising an interior and an exterior and including threads in said interior and which fits over said second end of said external shaft;
    (e) a tension member comprising an elastic spiral with a first coil and a last coil wherein said first coil is associated with said lower end of said internal shaft and said last coil is fixedly associated with said interior of said endpiece such that as said threads in said interior of said endpiece are turned on said external threads on said second end of said external shaft, said tension member is tightened;

(f) a trough-like cradle with a foot member comprising a first end affixed to said trough-like cradle, an aperture through a second end, said second end inserted in said internal shaft and secured in pivotal relationship with said internal shaft by a cotter through said set of aligned apertures in said internal shaft and said aperture through the second end of said foot member; and (g) a slidable marker frictionally engaged with said internal shaft for retaining a strength reading.

11. A stalk strength tester as claimed in claim 10 wherein said internal and external shafts and said trough-like cradle are made of PVC pipe.

12. A stalk strength tester comprising:

(a) an external shaft comprising a first end, and a second end;

(b) an internal shaft comprising an upper end, and a lower end;

(c) said lower end of said internal shaft is in telescopic relationship with said external shaft;

(d) means for slidably maintaining said internal shaft and said external shaft in telescopic relationship;

(e) a trough-like stalk cradle for pivotally aligning a stalk for strength measurement;

(f) means for pivotally associating said trough-like stalk cradle with said upper end of said internal shaft;

(g) means associated with said internal shaft and said external shaft to provide a measurement of the strength of a stalk.

\* \* \* \* \*